United States Patent [19]

Hesse

[11] Patent Number: Plant 6,331

[45] Date of Patent: Oct. 11, 1988

[54] CHRYSANTHEMUM PLANT NAMED SKYLIGHT

[75] Inventor: Peter S. Hesse, Bradenton, Fla.

[73] Assignee: Ball Pan Am Plant Company, Parrish, Fla.

[21] Appl. No.: 927,135

[22] Filed: Nov. 5, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A chrysanthemum plant named Skylight particularly characterized by its daisy flower form, bright lavender ray florets, good breaking habit, 55–65 mm capitulum diameter, and by its good keeping and shipping qualities.

1 Drawing Sheet

The present invention comprises a new and distinct cultivar of Chrysanthemum, botanically known as *Chrysanthemum morifolium,* Ramat., and referred to by the cultivar name Skylight.

Skylight is a product of a planned breeding program which had the objective of creating new chrysanthemum cultivars having daisy capitulum form, bright lavender ray floret color, freely breaking habit, good flower substance, and a nine week response. Such traits in combination were not present or needed improvement in previously available commercial cultivars.

Skylight was originated from a hybridization made by applicant in a controlled breeding program in West Chicago, Ill. in 1980. The female parent was Twilight, and the male parent of Skylight was Circus.

Skylight was discovered and selected as one flowering plant within the progeny of the stated parentage by Peter S. Hesse in November 1981 in a controlled environment in Parrish, Fla.

The first act of asexual reproduction of Skylight was accomplished when vegetative cuttings were taken from the initial selection in February 1982 in a controlled environment in Parrish, Fla. by a technician working under formulations established and supervised by Peter S. Hesse. Horticultural examination of selected units initiated in 1982 has demonstrated that the combination of characteristics as herein disclosed for Skylight are firmly fixed and are retained through successive generations of asexual reproduction.

Skylight has not been observed under all possible environmental conditions. The phenotype may vary significantly with variations in environment such as temperature, light intensity and day length. The following observations, measurements and comparisons describe plants grown in Parrish, Fla. under greenhouse conditions which approximate those generally used in commercial practice.

The following traits have been repeatedly observed and are determined to be basic characteristics of Skylight, which in combination distinguish this chrysanthemum as a new and distinct cultivar:

1. Nine week flowering response.
2. Bright lavender ray florets, some of which are rolled up at the base where attached to the receptacle, showing the pale lavender underside of the florets.
3. Capitulum diameter 55–65 mm across face.
4. Ray florets 25–35 mm long, 8–12 mm wide.
5. About 30–35 ray florets per capitulum.

6. Six to seven breaks per plant from one pinch.
7. Good keeping and shipping qualities.
8. Daisy capitulum form.

Of the many commercial cultivars known to the present inventor, the most similar in comparison to Skylight is Circus and Twilight. Reference is made to attached Chart A which compares certain characteristics of Skylight to those same characteristics of Circus. In general, the flowers of Skylight are slightly larger in diameter than Circus, and Skylight has better breaking than Twilight. Skylight performs better in the winter than Circus, but not as well as Twilight. When compared with Circus, Skylight has fewer ray florets, a more intense flower color, and its growth is more vigorous under Florida summer conditions. The flower form and type of Skylight are similar to those same characteristics of Circus and Twilight.

The accompanying photographic drawing shows typical inflorescence and foliage characteristics of Skylight, with colors being as nearly true as possible with illustrations of this type. The photograph is in black and white, with one flower being colored to accurately depict true ray and disc floret color.

In the following description, color references are made to The Royal Horticultural Society Colour Chart. The color values were determined at approximately 3:30 pm on July 21, 1986 under fluorescent light at Parrish, Fla.

Classification:

*Botanical.*—*Chrysanthemum morifolium,* Ramat., cv. Skylight

*Commercial.*—Daisy pot mum.

INFLORESCENCE

A. Capitulum:

*Form.*—Flat.

*Type.*—Single.

*Diameter across face.*—55–65 mm.

B. Corolla of ray florets:

*Color (general tonality from a distance of three meters).*—Bright lavender.

*Color (lower surface).*—77D.

*Color (upper surface).*—78B.

C. Corolla of disc florets:

*Color (mature).*—Yellow.

*Color* (immature).—Light yellow-green.

D. Reproductive organs:

*Androecium.*—Present in disc florets only.

*Gynoecium.*—Present in both ray and disc florets.

PLANT

A. General appearance:

*Height.*—26–33 cm from the edge of the pot.

B. Foliage:

*Color (upper surface).*—147A.

*Color (under surface).*—147B.

*Shape.*—Ovate, deeply lobed and slightly serrated.

CHART A

| | Skylight vs. Circus Summer Conditions | |
|---|---|---|
| | Skylight | Circus |
| Flower Diameter | up to 65 mm | up to 55 mm |
| Ray Floret Number | average 22 | average 31 |
| Mature Flower Color | 78 A | 77 D |
| Immature Flower | 74 A | 78 A |

CHART A-continued

| | Skylight vs. Circus Summer Conditions | |
|---|---|---|
| | Skylight | Circus |
| Color | | |

The plants of Skylight and Circus which were used in this comparison were grown together on the same bench in a greenhouse in Parrish, Fla. The color readings were taken under fluorescent light at 4:00 pm on Sept. 12, 1986.

Skylight in comparison to Circus has larger flowers, less ray florets, more intense flower color and its growth is more vigorous under Florida summer conditions.

I claim:

1. A new and distinct chrysanthemum plant named Skylight, as described and illustrated, and particularly characterized by its daisy flower form, bright lavender ray florets, good breaking habit, 55–65 mm capitulum diameter, and by its good keeping and shipping qualities.

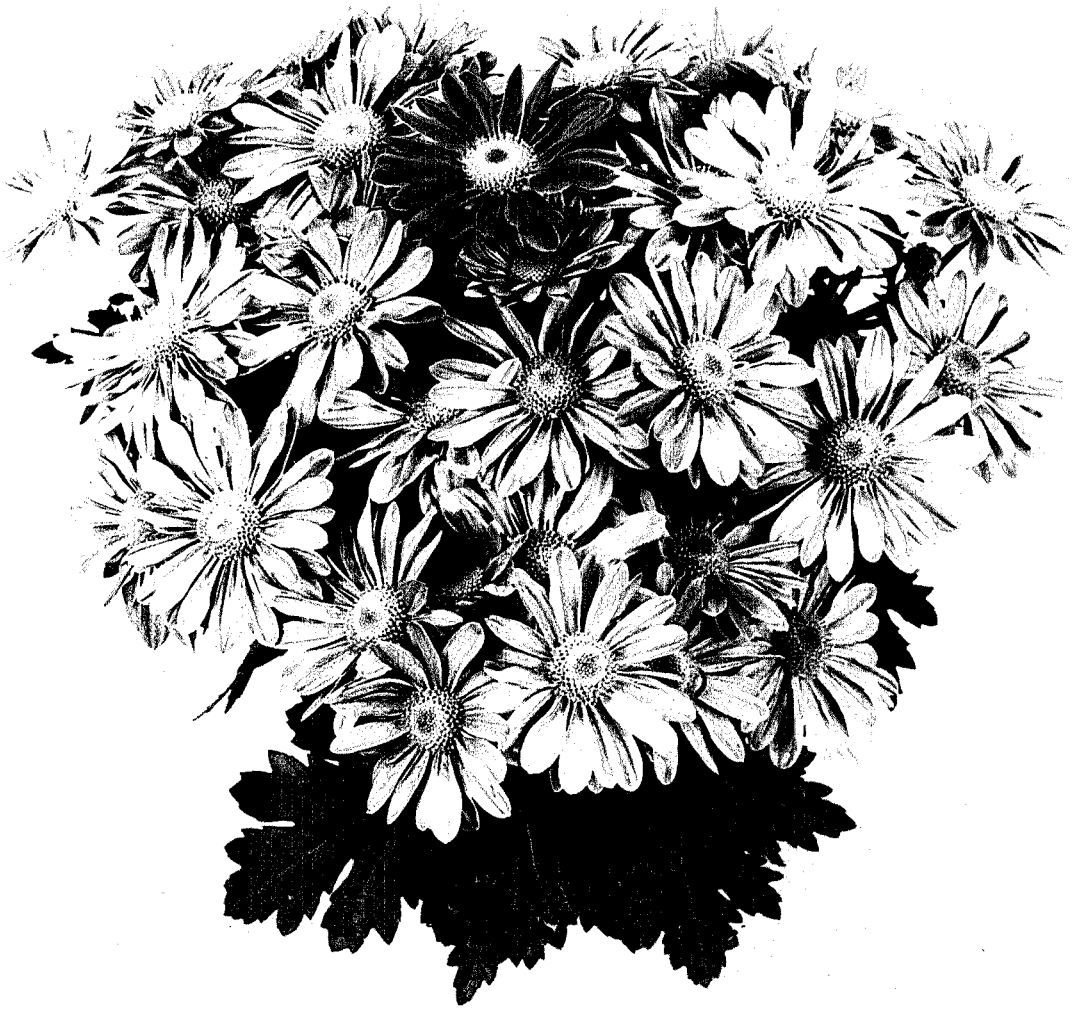

* * * * *